US009011887B2

(12) United States Patent
Chieffi et al.

(10) Patent No.: US 9,011,887 B2
(45) Date of Patent: Apr. 21, 2015

(54) ENCAPSULATE WITH A CATIONIC AND ANIONIC POLYMERIC COATING

(75) Inventors: Andre Chieffi, Tynemouth (GB); Julian David Martin, Newcastle upon Tyne (GB); John Smets, Lubbeek (BE); Jiten Odhavji Dihora, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 305 days.

(21) Appl. No.: 12/939,721

(22) Filed: Nov. 4, 2010

(65) Prior Publication Data

US 2011/0110993 A1   May 12, 2011

Related U.S. Application Data

(60) Provisional application No. 61/258,900, filed on Nov. 6, 2009, provisional application No. 61/258,874, filed on Nov. 6, 2009, provisional application No. 61/311,928, filed on Mar. 9, 2010.

(51) Int. Cl.

| | | |
|---|---|---|
| A61Q 5/12 | (2006.01) |
| C11D 3/50 | (2006.01) |
| C11D 17/00 | (2006.01) |
| A61Q 5/06 | (2006.01) |
| C11D 3/60 | (2006.01) |
| A61Q 19/00 | (2006.01) |
| A61K 9/00 | (2006.01) |
| A01N 25/28 | (2006.01) |
| A23L 1/00 | (2006.01) |
| A23L 1/22 | (2006.01) |
| A61K 8/11 | (2006.01) |
| A61K 8/73 | (2006.01) |
| A61K 8/81 | (2006.01) |
| B01J 13/22 | (2006.01) |
| C09B 67/02 | (2006.01) |

(52) U.S. Cl.
CPC ............ *C11D 17/0039* (2013.01); *A01N 25/28* (2013.01); *A23L 1/0029* (2013.01); *A23L 1/22016* (2013.01); *A61K 8/11* (2013.01); *A61K 8/731* (2013.01); *A61K 8/8147* (2013.01); *A61K 2800/412* (2013.01); *A61Q 19/00* (2013.01); *B01J 13/22* (2013.01); *C09B 67/0097* (2013.01); *C11D 3/505* (2013.01)

(58) Field of Classification Search
None
See application file for complete search history.

(56) References Cited

U.S. PATENT DOCUMENTS

| | | |
|---|---|---|
| 4,430,243 A | 2/1984 | Bragg |
| 4,515,705 A | 5/1985 | Moeddel |
| 4,537,706 A | 8/1985 | Severson, Jr. |
| 4,537,707 A | 8/1985 | Severson, Jr. |
| 4,550,862 A | 11/1985 | Barker et al. |
| 4,561,998 A | 12/1985 | Wertz et al. |
| 4,597,898 A | 7/1986 | Vander Meer |
| 4,968,451 A | 11/1990 | Scheibel et al. |
| 5,486,303 A | 1/1996 | Capeci et al. |
| 5,489,392 A | 2/1996 | Capeci et al. |
| 5,516,448 A | 5/1996 | Capeci et al. |
| 5,565,145 A | 10/1996 | Watson et al. |
| 5,565,422 A | 10/1996 | Del Greco et al. |
| 5,569,645 A | 10/1996 | Dinniwell et al. |
| 5,574,005 A | 11/1996 | Welch et al. |
| 5,576,282 A | 11/1996 | Miracle et al. |
| 5,595,967 A | 1/1997 | Miracle et al. |
| 5,597,936 A | 1/1997 | Perkins et al. |
| 5,691,297 A | 11/1997 | Nassano et al. |
| 5,879,584 A | 3/1999 | Bianchetti et al. |
| 5,929,022 A | 7/1999 | Velazquez |
| 6,132,558 A | 10/2000 | Dyllick-Brenzinger et al. |
| 6,225,464 B1 | 5/2001 | Hiler, II et al. |
| 6,294,514 B1 | 9/2001 | Welling |
| 6,306,812 B1 | 10/2001 | Perkins et al. |
| 6,326,348 B1 | 12/2001 | Vinson et al. |
| 6,376,445 B1 | 4/2002 | Bettiol et al. |
| 6,544,926 B1 | 4/2003 | Bodmer et al. |
| 6,592,990 B2 | 7/2003 | Schwantes |
| 6,869,923 B1 | 3/2005 | Cunningham et al. |
| 1,797,947 A1 | 6/2007 | Anastasiou et al. |
| 2003/0109401 A1 | 6/2003 | Housmekerides et al. |
| 2005/0153135 A1* | 7/2005 | Popplewell et al. ........ 428/402.2 |
| 2006/0039934 A1* | 2/2006 | Ness et al. .................... 424/401 |
| 2006/0287205 A1 | 12/2006 | Popplewell et al. |

(Continued)

FOREIGN PATENT DOCUMENTS

| | | |
|---|---|---|
| EP | 1 533 364 A2 | 5/2005 |
| JP | 1 168337 A | 7/1989 |

(Continued)

OTHER PUBLICATIONS

"Agglomerate" from the Collins English Dictionary, http://www.xreferplus.com/entry/hcengdict/agglomerate, accessed Feb. 3, 2012.*

(Continued)

*Primary Examiner* — Kortney L Klinkel
*Assistant Examiner* — Melissa Javier
(74) *Attorney, Agent, or Firm* — James F. McBride; Steven W. Miller

(57) ABSTRACT

The present application relates to high efficiency particles and compositions, such as consumer products, comprising such high efficiency particles as well as processes for making and using such high efficiency particles and compositions comprising such high efficiency particles. Such high efficiency particles and compositions provide enhanced benefit agent delivery to a situs that is treated with such high efficiency particles and compositions.

14 Claims, No Drawings

(56) References Cited

U.S. PATENT DOCUMENTS

| | | |
|---|---|---|
| 2007/0123442 A1 | 5/2007 | Holzner et al. |
| 2007/0202063 A1 | 8/2007 | Dihora et al. |
| 2007/0233026 A1 | 10/2007 | Roe et al. |
| 2008/0206291 A1* | 8/2008 | Ouali et al. .................... 424/401 |
| 2009/0209661 A1 | 8/2009 | Somerville Roberts et al. |
| 2009/0226529 A1 | 9/2009 | Quellet et al. |
| 2009/0247449 A1 | 10/2009 | Burdis et al. |
| 2010/0305021 A1 | 12/2010 | Dykstra |
| 2011/0086788 A1 | 4/2011 | Smets et al. |
| 2011/0107524 A1 | 5/2011 | Chieffi et al. |
| 2011/0110997 A1 | 5/2011 | Cunningham et al. |
| 2011/0111999 A1 | 5/2011 | Smets et al. |

FOREIGN PATENT DOCUMENTS

| | | |
|---|---|---|
| WO | WO 00/32601 A2 | 6/2000 |
| WO | WO 01/41915 A1 | 6/2001 |
| WO | WO 01/87475 A1 | 11/2001 |

OTHER PUBLICATIONS

International Search Report; International Application No. PCT/US2010/055340; date of mailing Feb. 25, 2011; 5 pages.

* cited by examiner ued States Patent

ENCAPSULATE WITH A CATIONIC AND ANIONIC POLYMERIC COATING

CROSS-REFERENCES TO RELATED APPLICATIONS

This application claims priority under 35 U.S.C. §119(e) to U.S. Provisional Application Ser. No. 61/258,900, filed Nov. 6, 2009, U.S. Provisional Application Ser. No. 61/258,874, filed Nov. 6, 2009, and U.S. Provisional Application Ser. No. 61/311,928, filed Mar. 9, 2010.

FIELD OF INVENTION

The present application relates to high efficiency particles and compositions, such as consumer products, comprising such high efficiency particles as well as processes for making and using such high efficiency particles and compositions comprising such high efficiency particles.

BACKGROUND OF THE INVENTION

Benefit agents, such as perfumes, silicones, waxes, flavors, vitamins and fabric softening agents, are expensive and/or generally less effective when employed at high levels in consumer products, for example, personal care compositions, cleaning compositions, and fabric care compositions. As a result, there is a desire to maximize the effectiveness of such benefit agents. One method of achieving such objective is to improve the delivery efficiencies of such benefit agents. Unfortunately, it is difficult to improve the delivery efficiencies of benefit agents as such agents may be lost do to the agents' physical or chemical characteristics, or such agents may be incompatible with other compositional components or the situs that is treated.

One method of improving the delivery efficiency of a benefit agent is to encapsulate such benefit agent. While such efforts may improve the delivery efficiency of the benefit agent, further delivery efficiency improvements are desired as encapsulated benefit agents may be lost before or after they are applied to the situs of interest due to factors such as mechanical or chemical interactions, for example the action of wash and or rinse liquors, and/or charge interactions. Accordingly, there is a need for a benefit agent containing delivery particle and compositions comprising same that provide improved benefit agent delivery efficiency.

SUMMARY OF THE INVENTION

The present application relates to high efficiency particles and compositions, such as consumer products, comprising such high efficiency particles as well as processes for making and using such high efficiency particles and compositions comprising such high efficiency particles.

DETAILED DESCRIPTION OF THE INVENTION

Definitions

As used herein "consumer product" means baby care, beauty care, fabric & home care, family care, feminine care, health care, snack and/or beverage products or devices generally intended to be used or consumed in the form in which it is sold. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for and/or methods relating to treating fabrics, hard surfaces and any other surfaces in the area of fabric and home care, including: air care including air fresheners and scent delivery systems, car care, dishwashing, fabric conditioning (including softening and/or freshing), laundry detergency, laundry and rinse additive and/or care, hard surface cleaning and/or treatment including floor and toilet bowl cleaners, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein, the term "cleaning and/or treatment composition" is a subset of consumer products that includes, unless otherwise indicated, beauty care, fabric & home care products. Such products include, but are not limited to, products for treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for treating fabrics, hard surfaces and any other surfaces in the area of fabric and home care, including: air care including air fresheners and scent delivery systems, car care, dishwashing, fabric conditioning (including softening and/or freshing), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners including toilet bowl cleaners; hair shampoos and hair-rinses; shower gels, fine fragrances and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists all for consumer or/and institutional use; and/or methods relating to oral care including toothpastes, tooth gels, tooth rinses, denture adhesives, tooth whitening.

As used herein, the term "fabric and/or hard surface cleaning and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, car or carpet shampoos, bathroom cleaners including toilet bowl cleaners; and metal cleaners, fabric conditioning products including softening and/or freshing that may be in liquid, solid and/or dryer sheet form; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists. All of such products which are applicable may be in standard, concentrated or even highly concentrated form even to the extent that such products may in certain aspect be non-aqueous.

As used herein, articles such as "a" and "an" when used in a claim, are understood to mean one or more of what is claimed or described.

As used herein, the terms "include", "includes" and "including" are meant to be non-limiting.

As used herein, the term "solid" includes granular, powder, bar and tablet product forms.

As used herein, the term "fluid" includes liquid, gel, paste and gas product forms.

As used herein, the term "situs" includes paper products, fabrics, garments, hard surfaces, hair and skin.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

High Efficiency Encapsulates

In one aspect, an encapsulate comprising a core, a shell having an inner and outer surface and a coating, said shell encapsulating said core, said coating coating the outer surface of said shell, said coating comprising a cationic polymer and an anionic polymer is disclosed.

In one aspect of said encapsulate said cationic polymer may comprise a moiety selected from the group consisting of a quaternary ammonium, a protonated primary amine, a protonated secondary amine, a protonated tertiary amine and combinations thereof; and said anionic polymer may comprise a moiety selected from the group consisting of an unprotonated carboxylic group, an unprotonated alcohol group, an unprotonated thiol group, an unprotonated primary amine, an unprotonated secondary amine and combinations thereof.

In one aspect of said encapsulate said cationic polymer may comprise a material selected from the group consisting of:
(i) a protein, for example a poly peptide;
(ii) a polysaccharide, said polysaccharide may comprise a material selected from the group consisting of starch, guar, cellulose and mixtures thereof, in one aspect said cellulose may comprise hydroxylethyl cellulose
(iii) a polyamide;
(iv) a poly(metha)acrylamide;
(v) a polyether;
(vi) a polyester;
(vii) a polyoxymethylene;
(viii) a silicone;
(ix) a polyurethane;
(x) a polyvinylether;
(xi) a polyethylene (propylene) oxide;
(xii) a polyvinyl alcohol;
(xiii) a polyvinyl acetate;
(xiv) a polyvinyl formal;
(xv) a polyvinyl butyral;
(xvi) a polyvinylmethylether;
(xvii) a polyvinylpyrrolidone;
(xviii) a polyvinylmethyl oxazolidone;
(xix) a polyvinylamine;
(xx) a polyvinylpyridine;
(xxi) a polyimidazoline;
(xxii) a poly(diallyldimethylammonium chloride) (DAMAC);
(xxiii) poly(N,N-dimethyl-3,5-methylenepiperidimium chloride);
(xxiv) copolymers of polyvinylamine and polyvinylalcohol
(xxi) oligimers of amines, in one aspect a diethylenetriamine, ethylene diamine, bis(3-aminopropyl)piperazine, N,N-Bis-(3-aminopropyl)methylamine, tris(2-aminoethyl)amine and mixtures thereof;
(xxv) a polyethyleneimine
(xxvi) a derivatized polyethyleneimine, for example, an ethoxylated polyethyleneimine;
(xxvii) a cationic surfactant, suitable cationic surfactants are disclosed below;
(xxviii) a polymeric compound comprising, at least two moieties selected from the moieties consisting of a carboxylic acid moiety, an amine moiety, a hydroxyl moiety, and a nitrile moiety on a backbone of polybutadiene, polyisoprene, polybutadiene/styrene, polybutadiene/acrylonitrile, carboxyl-terminated polybutadiene/acrylonitrile or combinations thereof; and
(xxiv) mixtures and/or co-polymers of (i)-(xxviii); and
b) said anionic polymer may comprise a material selected from the group consisting of:
(i) a protein, for example, a poly peptide;
(ii) a polysaccharide, in one aspect, said polysaccharide may comprise a material selected from the group consisting of starch, guar, cellulose and mixtures thereof, in one aspect said cellulose comprises carboxylmethyl cellulose
(iii) a polyamide;
(iv) a poly(metha)acrylamide;
(v) a polyether;
(vi) a polyester;
(vii) a polyoxymethylene;
(viii) a silicone;
(ix) a polyurethane;
(x) a polyvinylether;
(xi) a polyethylene(propylene)oxide;

(xii) a polyvinyl alcohol;
(xiii) a polyvinyl acetate;
(xiv) a polyvinyl formal;
(xv) a polyvinyl butyral;
(xvi) a polyvinylmethylether;
(xvii) a polyvinylpyrrolidone;
(xviii) a polyvinylmethyl oxazolidone;
(xix) a polyvinylamine;
(xx) a polyvinylpyridine;
(xxii) a polyacrylate,
(xxiii) copolymers of polyvinylamine and polyvinylalcohol
(xxiv) a polymeric compound that may comprise, at least two moieties selected from the moieties consisting of a carboxylic acid moiety, an amine moiety, a hydroxyl moiety, and a nitrile moiety on a backbone of polybutadiene, polyisoprene, polybutadiene/styrene, polybutadiene/acrylonitrile, carboxyl-terminated polybutadiene/acrylonitrile or combinations thereof; and
(xxv) mixtures and/or co-polymers of (i)-(xxiv).

In one aspect of said encapsulate said cationic polymer may comprise a material selected from the group consisting of a poly peptide, a starch, a guar, a cellulose and mixtures thereof; and said anionic polymer may comprise a material selected from the group consisting of: a poly peptide, a starch, a guar, a cellulose and mixtures thereof.

In one aspect of said encapsulate, said cationic polymer may comprise hydroxylethyl cellulose; and said anionic polymer may comprise carboxylmethyl cellulose.

In one aspect of said encapsulate, said core may comprise a material selected from the group consisting of perfumes; brighteners; dyes; insect repellants; silicones; waxes; flavors; vitamins; fabric softening agents; skin care agents in one aspect, paraffins; enzymes; anti-bacterial agents; bleaches; sensates; and mixtures thereof; and said shell may comprise a material selected from the group consisting of polyethylenes; polyamides; polystyrenes; polyisoprenes; polycarbonates; polyesters; polyacrylates; aminoplasts, in one aspect said aminoplast may comprise a polyureas, polyurethane, and/or polyureaurethane, in one aspect said polyurea may comprise polyoxymethyleneurea and/or melamine formaldehyde; polyolefins; polysaccharides, in one aspect said polysaccharide may comprise alginate and/or chitosan; gelatin; shellac; epoxy resins; vinyl polymers; water insoluble inorganics; silicone; and mixtures thereof.

In one aspect of said encapsulate, said core may comprise perfume.

In one aspect of said encapsulate, said shell may comprise melamine formaldehyde and/or cross linked melamine formaldehyde.

In one aspect of said encapsulate, said encapsulate may comprise, based on total encapsulate weight, from about 0.1% to about 80% of said coating, from about 1% to about 25% of said coating, or even from about 5% to about 10% of said coating.

In one aspect of said encapsulate, the ratio of said cationic polymer to said anionic polymer may be from about 99.95:0.05 to about 0.05:99.95, from about 9:1 to about 1:9, from about 5:1 to about 1:5, from about 2:1 to about 1:2, or even about 1:1.

In one aspect of said encapsulate, said encapsulate comprising, based on total encapsulate weight, from about 1% to about 25% of said coating and the ratio of said cationic polymer to said anionic polymer being from about 5:1 to about 1:5.

Suitable cationic surfactants may comprise, as the principal active, compounds of the following formula:

$$\{R_{4-m}-N^+-[X-Y-R^1]_m\}X^- \qquad (1)$$

wherein each R comprises either hydrogen, a short chain $C_1$-$C_6$, in one aspect a $C_1$-$C_3$ alkyl or hydroxyalkyl group, for example methyl, ethyl, propyl, hydroxyethyl, and the like, poly($C_{2-3}$ alkoxy), polyethoxy, benzyl, or mixtures thereof; each X is independently $(CH_2)n$, $CH_2-CH(CH_3)-$ or $CH-(CH_3)-CH_2-$; each Y may comprise $-O-(O)C-$, $-C(O)-O-$, $-NR-C(O)-$, or $-C(O)-NR-$; each m is 2 or 3; each n is from 1 to about 4, in one aspect 2; the sum of carbons in each $R^1$, plus one when Y is $-O-(O)C-$ or $-NR-C(O)-$, may be $C_{12}$-$C_{22}$, or $C_{14}$-$C_{20}$, with each $R^1$ being a hydrocarbyl, or substituted hydrocarbyl group; and $X^-$ may comprise any softener-compatible anion. In one aspect, the softener-compatible anion may comprise chloride, bromide, methylsulfate, ethylsulfate, sulfate, and nitrate. In another aspect, the softener-compatible anion may comprise chloride or methyl sulfate.

A second type of cationic surfactant may have the formula:

$$[R_{4-m}-N^+-R^1_m]X^- \qquad (2)$$

wherein each R, $R^1$, m and $X^-$ have the same meanings as before.

Non-limiting examples of cationic surfactants that may comprise Formula (1) are N,N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl) N-(2 hydroxyethyl) N-methyl ammonium methylsulfate.

Non-limiting examples of cationic surfactants that may comprise Formula (2) include dialkylenedimethylammonium salts such as dicanoladimethylammonium chloride, di(hard)tallowedimethylammonium chloride dicanoladimethylammonium methylsulfate. An example of commercially available dialkylenedimethylammonium salts usable in the present invention is dioleyldimethylammonium chloride available from Witco Corporation under the trade name Adogen® 472 and dihardtallow dimethylammonium chloride available from Akzo Nobel Arquad 2HT75.

In one aspect, suitable polyamines include Lupasol® WF, SK, PS, PO100, P, HF, G500, G35, G20 water free, G20, G100, FG, FC, and PR8515 products supplied by BASF of Ludwigshaven, Germany. In another aspect, suitable polymeric materials encompass amine terminated, epoxy terminated, or vinyl terminated polymers. Suitable molecular weights for these polymers range from about 1,000 to about 10,000,000. In one aspect, the suitable polymers may have molecular weights that range from about 1,000 to about 10,000,000 or from about 2,000 to about 50,000. Suitable polymeric materials are available from NOVEON (Cleveland, Ohio U.S.A) and SARTOMER (Philadelphia, Pa. U.S.A.). Such materials include HYCAR® materials CTB 2000x162, CTBNX 1300x18, CTBNX 1300x9, CTBN 1300x8, CTBN 1300x31, ATB 2000x173, ATBN 1300x21, ATBN 1300x16, ATBN 1300x45, ATBN 1300x35, ATBN 1300x42, VTB 2000x168, VTBNX1300x33, VTBNX1300x43, ETBN 1300x40, and ETBN 1300x44 from NOVEON or Emerald Performance Materials of Cuyahoga Falls, Ohio U.S.A. and Krasol® LBH 5000 from SARTOMER.

Suitable capsules that can be turned into the high efficiency encapsules disclosed herein can be made in accordance with Applicants' teaching including but not limited to Applicants' examples, the teaching of USPA 2008/0305982 A1 and/or USPA 2009/0247449 A1. Alternatively, suitable capsules can be purchased from Appleton Papers Inc. of Appleton, Wis. USA.

In addition, the materials for making the aforementioned encapsulates can be obtained from CP Kelco Corp. of San Diego, Calif., USA; BASF AG of Ludwigshafen, Germany; Rhodia Corp. of Cranbury, N.J., USA; Hercules Corp. of Wilmington, Del., USA; Agrium Inc. of Calgary, Alberta, Canada, ISP of New Jersey U.S.A., Akzo Nobel of Chicago, Ill., USA; Stroever Shellac Bremen of Bremen, Germany; Dow Chemical Company of Midland, Mich., USA; Bayer AG of Leverkusen, Germany; Sigma-Aldrich Corp., St. Louis, Mo., USA Process of Making Encapsulates In one aspect, the encapsulates that are disclosed herein may be made in accordance with Applicants' teachings including, but not limited to, Applicants' examples.

In one aspect, a process of making a coated encapsulate that may comprise:
a) combining an encapsulate, a plasticizer, a coating material that may comprise a cationic polymer and an anionic polymer and, optionally, a binder and/or chelant to form a mixture;
b) combining said mixture with said dusting agent to form a material; and
c) removing a sufficient amount of said plasticizer from said material to yield a product that may comprise, based on total product weight from about 1% to about 50% plasticizer is disclosed.

In one aspect of said process:
a) said encapsulate may comprise a core comprising perfume;
b) said plasticizer may comprise water;
c) said cationic polymer may comprise a polysaccharide;
d) an anionic polymer may comprise a polysaccharide; and
e) said dusting agent may comprise silica.

In one aspect of said process said cationic polymer may comprise hydroxylethyl cellulose and an anionic polymer may comprise carboxylmethyl cellulose.

Agglomerate

In one aspect, an agglomerate that may comprise any of the capsules disclosed herein is disclosed. Such agglomerate may be made by any suitable agglomerating technique including, but not limited to, the techniques disclosed Applicants' examples and USPA 2009/0209661 A1.

Consumer Product

In one aspect, a consumer product comprising any of the capsules disclosed herein and/or agglomerates comprising such encapsulates as well as an adjunct ingredient is disclosed.

In one aspect of said consumer product, said consumer product may be a cleaning and/or treatment composition.

In one aspect of said consumer product, said consumer product may be a laundry detergent and/or fabric softener.

In one aspect of said consumer product, said consumer product may be solid detergent that may comprise any agglomerate disclosed herein and an adjunct ingredient.

In one aspect, the agglomerated encapsulates (agglomerate) disclosed herein are suitable for use in consumer products, cleaning and treatment compositions and fabric and hard surface cleaning and/or treatment compositions, detergents, and highly compacted consumer products, including highly compacted fabric and hard surface cleaning and/or treatment compositions, for example highly compacted detergents that may be solids or fluids, at levels, based on total consumer product weight, from about 0.001% to about 20%, from about 0.01% to about 10%, from about 0.05% to about 5%, from about 0.1% to about 2%.

In addition to the encapsulates disclosed herein, certain perfume delivery systems may be used in the aforementioned compositions. Methods of making such perfume delivery systems and methods of making such perfume delivery systems are disclosed in USPA 2007/0275866 A1. Such perfume delivery systems include: Polymer Assisted Delivery (PAD), Molecule-Assisted Delivery (MAD), Fiber-Assisted Delivery (FAD), Amine Assisted Delivery (AAD), Cyclodextrin Delivery System (CD), Starch Encapsulated Accord (SEA), Inorganic Carrier Delivery System (ZIC), Pro-Perfume (PP). Such perfume delivery systems may be used in any combination in any type of consumer product, cleaning and/or treatment composition, fabric and hard surface cleaning and/or treatment composition, detergent, and highly compact detergent.

Adjunct Materials

For the purposes of the present invention, the non-limiting list of adjuncts illustrated hereinafter are suitable for use in the instant compositions and may be desirably incorporated in certain embodiments of the invention, for example to assist or enhance performance, for treatment of the substrate to be cleaned, or to modify the aesthetics of the composition as is the case with perfumes, colorants, dyes or the like. It is understood that such adjuncts are in addition to the components that are supplied via Applicants' encapsulates and agglomerates. The precise nature of these additional components, and levels of incorporation thereof, will depend on the physical form of the composition and the nature of the operation for which it is to be used. Suitable adjunct materials include, but are not limited to, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

Each adjunct ingredients is not essential to Applicants' compositions. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids and/or pigments. However, when one or more adjuncts are present, such one or more adjuncts may be present as detailed below:

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—The compositions of the present invention can comprise one or more detergent builders or builder systems.

When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra(methyl-enephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include manganese, iron and chromium. Suitable MRL's herein are a special type of ultra-rigid ligand that is cross-bridged such as 5,12-diethyl-1,5,8,12-tetraazabicyclo[6.6.2]hexa-decane.

Suitable transition metal MRLs are readily prepared by known procedures, such as taught for example in WO 00/32601, and U.S. Pat. No. 6,225,464.

Method of Use

Certain of the consumer products disclosed herein can be used to clean or treat a situs inter alia a surface or fabric. Typically at least a portion of the situs is contacted with an embodiment of Applicants' composition, in neat form or diluted in a liquor, for example, a wash liquor and then the situs may be optionally washed and/or rinsed. In one aspect, a situs is optionally washed and/or rinsed, contacted with a particle according to the present invention or composition comprising said particle and then optionally washed and/or rinsed. In one aspect, a method of cleaning or treating a situs comprising optionally washing and/or rinsing said situs, contacting said situs with the composition selected from the compositions and mixtures thereof disclosed herein and optionally washing and/or rinsing said situs is disclosed. For purposes of the present invention, washing includes but is not limited to, scrubbing, and mechanical agitation. The fabric may comprise most any fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Example 1

80% Core/20 wt % Wall Melamine Based Polyurea Capsule

A first mixture is prepared by combining 208 grams of water and 5 grams of alkyl acrylate-acrylic acid copolymer (Polysciences, Inc. of Warrington, Pa., USA). This first mixture is adjusted to pH 5.0 using acetic acid. 125 grams of the capsule core material comprising a fragrance oil is added to the first mixture at a temperature of 45° C. to form an emulsion. The ingredients to form the capsule wall material are prepared as follows: 9 grams of a corresponding capsule wall material copolymer pre-polymer (butylacrylate-acrylic acid copolymer) and 90 grams of water are combined and adjusted to pH 5.0. To this mixture is added 28 grams of a partially methylated methylol melamine resin solution ("Cymel 385", 80% solids, Cytec). This mixture is added to the above described fragrance oil-in-water emulsion with stirring at a temperature of 45 degrees Centigrade. High speed blending is used to achieve a volume-mean particle size of 15 micron. The temperature of the mixture is gradually raised to 65 degrees Centigrade, and is maintained at this temperature overnight with continuous stirring to initiate and complete encapsulation. To form the acrylic acid-alkyl acrylate copolymer capsule wall, the alkyl group can be selected from ethyl, propyl, butyl, amyl, hexyl, cyclohexyl, 2-ethylhexyl, or other alkyl groups having from one to about sixteen carbons, preferably one to eight carbons.

Example 2

Agglo with CMC CatHEC

A 9 kg aliquot of perfume microcapsule slurry of Examples 1 or 2 is mixed using a Eurostar mixer (IKA) with a R1382 attachment at a constant speed of 200 RPM. To the aliquot 300 g of carboxymethyl cellulose (CP Kelco) and 300 g of CatHEC (DOW) is added while mixing using the Eurostar mixer with same attachment and speed as described above. The slurry is mixed for a total of two hours or until a uniform paste is formed.

Example 3

Agglo with CMC and CatHEC Containing Chelant

A 9 kg aliquot of perfume microcapsule slurry of Examples 1 or 2 is mixed using a Eurostar mixer (IKA) with a R1382 attachment at a constant speed of 200 RPM. To the aliquot, 5.4 g of ethylenediaminedisuccinicacid (EDDS), followed by 300 g of carboxymethyl cellulose (CP Kelco) and 300 g of CatHEC (DOW) is added while mixing using the Eurostar mixer with same attachment and speed as described above. The slurry is mixed for a total of two hours or until a uniform paste is formed.

Example 4

A 9 kg aliquot of perfume microcapsule slurry of Examples 2 is mixed using a Eurostar mixer (IKA) with a R1382 attachment at a constant speed of 200 RPM. To the aliquot 500 g of carboxymethyl cellulose (CP Kelco) is added while mixing using the Eurostar mixer with same attachment and speed as described above. The slurry is mixed for a total of two hours or until a uniform paste is formed.

Example 5

1.28 kg of precipitated silica Sipernat® 22S (Degussa) is added to a F-20 paddle mixer (Forberg). The mixer is run initially for 5 seconds to distribute the silica evenly on the base of the mixer. The mixer is stopped and 8.25 kg of paste, made according to Example 3 or 4, is evenly distributed onto the powder. The mixer is then run at 120 rpm for a total of 30 seconds. Following mixing, the wet particles are dumped out of the mixer and screened using a 2000 micron sieve to remove the oversize. The product passing through the screen is dried in 500 g batches in a CDT 0.02 fluid bed dryer (Niro) to a final moisture content of 20 wt % measured by Karl Fischer. The dryer is operated at an inlet temperature of 140° C. and air velocity of 0.68 m/s.

Examples 6-13

Examples of laundry detergent compositions comprising the perfume composition are included below.

| Raw material | % w/w of laundry detergent compositions ||||||||
|---|---|---|---|---|---|---|---|---|
| | 6 | 7 | 8 | 9 | 10 | 11 | 12 | 13 |
| Linear alkyl benzene sulphonate | 7.1 | 6.7 | 11.0 | 10.6 | 6.9 | 4.5 | 10.1 | 8.9 |
| Sodium $C_{12-15}$ alkyl ethoxy sulphate having a molar average degree of ethoxylation of 3 | 3.5 | 0.0 | 1.5 | 0.0 | 0.0 | 0.0 | 0.0 | 1.9 |
| Acrylic Acid/Maleic Acid Copolymer | 3.6 | 1.8 | 4.9 | 2.0 | 1.0 | 1.6 | 3.9 | 2.3 |
| Sodium Alumino Silicate (Zeolite 4A) | 4.0 | 0.5 | 0.8 | 1.4 | 16.3 | 0.0 | 17.9 | 2.4 |
| Sodium Tripolyphosphate | 0.0 | 17.5 | 0.0 | 15.8 | 0.0 | 23.3 | 0.0 | 0.0 |
| Sodium Carbonate | 23.2 | 16.8 | 30.2 | 17.3 | 18.4 | 9.0 | 20.8 | 30.0 |
| Sodium Sulphate | 31.4 | 29.4 | 35.5 | 7.2 | 26.3 | 42.8 | 33.2 | 28.3 |
| Sodium Silicate | 0.0 | 4.4 | 0.0 | 4.5 | 0.0 | 6.1 | 0.0 | 4.6 |
| $C_{14-15}$ alkyl ethoxylated alcohol having a molar average degree of ethoxylation of 7 | 0.4 | 2.6 | 0.8 | 2.5 | 3.1 | 0.3 | 3.8 | 0.4 |
| Sodium Percarbonate | 16.0 | 0.0 | 8.4 | 20.4 | 13.1 | 3.6 | 0.0 | 7.0 |
| Sodium Perborate | 0.0 | 9.9 | 0.0 | 0.0 | 0.0 | 0.0 | 0.0 | 0.0 |
| Tetraacetylethylenediamine (TAED) | 2.2 | 1.7 | 0.0 | 4.7 | 3.6 | 0.0 | 0.0 | 0.8 |
| Calcium Bentonite | 0.0 | 0.0 | 0.0 | 1.8 | 0.0 | 0.0 | 0.0 | 5.6 |
| Citric acid | 2.0 | 1.5 | 2.0 | 2.0 | 2.5 | 1.0 | 2.5 | 1.0 |
| Protease (84 mg active/g) | 0.14 | 0.12 | 0.0 | 0.12 | 0.09 | 0.08 | 0.10 | 0.08 |
| Amylase (22 mg active/g) | 0.10 | 0.11 | 0.0 | 0.10 | 0.10 | 0.0 | 0.14 | 0.08 |

-continued

| Raw material | % w/w of laundry detergent compositions | | | | | | | |
|---|---|---|---|---|---|---|---|---|
| | 6 | 7 | 8 | 9 | 10 | 11 | 12 | 13 |
| Lipase (11 mg active/g) | 0.70 | 0.50 | 0.0 | 0.70 | 0.50 | 0.0 | 0.0 | 0.0 |
| Cellulase (2.3 mg active/g) | 0.0 | 0.0 | 0.0 | 0.0 | 0.0 | 0.0 | 0.18 | 0.0 |
| Benefit agent composition of Example 3 | 1.4 | 0.6 | 0.8 | 1.0 | 0.7 | 0.3 | 0.7 | 1.2 |
| Water & Miscellaneous | Balance to 100% | | | | | | | |

The equipment and materials described in Examples 1 through to 19 can be obtained from the following: IKA Werke GmbH & Co. KG, Staufen, Germany; CP Kelco, Atlanta, United States; Forberg International AS, Larvik, Norway; Degussa GmbH, Düsseldorf, Germany; Niro A/S, Soeberg, Denmark; Baker Perkins Ltd, Peterborough, United Kingdom; Nippon Shokubai, Tokyo, Japan; BASF, Ludwigshafen, Germany; Braun, Kronberg, Germany; Industrial Chemicals Limited, Thurrock, United Kingdom; Primex ehf, Siglufjordur, Iceland; ISP World Headquarters; Polysciences, Inc. of Warrington, Pa., United States; Cytec Industries Inc., New Jersey, United States; International Specialty Products, Wayne, N.J., United States; P&G Chemicals Americas, Cincinnati, Ohio, United States; Sigma-Aldrich Corp., St. Louis, Mo., United States, Dow Chemical Company of Midland, Mich., USA The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An encapsulate comprising a core, a shell having an inner and outer surface, and a coating, said shell encapsulating said core, said coating coating the outer surface of said shell, said coating comprising a cationic polymer comprising hydroxyl ethyl cellulose and an anionic polymer comprising carboxyl methyl cellulose, wherein the ratio of the cationic polymer to the anionic polymer is from about 5:1 to about 1:5 by weight, and wherein the encapsulate comprises, based on total encapsulate weight, from about 1% to about 25% of the coating.

2. The encapsulate of claim 1 wherein;
  a) said core comprises a material selected from the group consisting of perfumes; brighteners; dyes; insect repellants; silicones; waxes; flavors; vitamins; fabric softening agents; skin care agents; enzymes; anti-bacterial agents; bleaches; sensates; and mixtures thereof;
  b) said shell comprises a material selected from the group consisting of polyethylenes; polyamides; polystyrenes; polyisoprenes; polycarbonates; polyesters; polyacrylates; aminoplasts; polyolefins; polysaccharides; gelatin; shellac; epoxy resins; vinyl polymers; water insoluble inorganics; silicone; and mixtures thereof.

3. The encapsulate of claim 2 wherein the skin care agent comprises paraffins.

4. The encapsulate of claim 2 wherein said aminoplast comprises polyureas, polyurethane, and/or polyureaurethane.

5. The encapsulate of claim 4 wherein said polyurea comprises polyoxymethyleneurea and/or melamine formaldehyde.

6. The encapsulate of claim 2 wherein said polysaccharides comprises alginate and/or chitosan.

7. The encapsulate of claim 1 wherein said core comprises perfume.

8. The encapsulate of claim 7 wherein said shell comprises melamine formaldehyde and/or cross linked melamine formaldehyde.

9. An agglomerate comprising the encapsulate of claim 1.

10. A consumer product comprising the encapsulate of claim 1 and an adjunct ingredient.

11. The consumer product of claim 10, said consumer product being a cleaning and/or treatment composition.

12. The consumer product of claim 10, said consumer product being a laundry detergent and/or fabric softener.

13. A solid detergent comprising the agglomerate of claim 9 and an adjunct ingredient.

14. A method of cleaning or treating a surface or fabric comprising optionally washing and/or rinsing said surface or fabric, contacting said surface or fabric with the composition of claim 1 and optionally washing and/or rinsing said surface or fabric.

* * * * *